United States Patent [19]

Wong

[11] Patent Number: 4,636,380

[45] Date of Patent: Jan. 13, 1987

[54] NOVEL PHYSIOLOGIC CHEMICAL METHOD OF LABELING PROTEIN SUBSTANCES WITH THE RADIONUCLIDES OF INDIUM

[76] Inventor: Dennis W. Wong, 2853 Sunnyglen Rd., Torrance, Calif. 90505

[21] Appl. No.: 602,923

[22] Filed: Apr. 23, 1984

[51] Int. Cl.$^4$ .................... A61K 43/00; A61K 49/00
[52] U.S. Cl. .................................... 424/1.1; 424/9; 534/10; 556/1; 556/28; 556/81
[58] Field of Search ............... 424/1.1, 9; 260/429 J, 260/429.7; 556/1, 28, 81

[56] References Cited

U.S. PATENT DOCUMENTS

| | | | |
|---|---|---|---|
| 4,335,095 | 6/1982 | Kelly | 424/1.1 |
| 4,485,086 | 11/1984 | Wong | 424/1.1 |
| 4,497,791 | 2/1985 | Gamble et al. | 424/1.1 |

*Primary Examiner*—Christine M. Nucker

[57] ABSTRACT

A novel chemical method of labeling plasma proteins, compounds and substances containing proteins with the radionuclides of indium at physiologic pH 6-8 condition producing an efficiently labeled radioactive tracer material suitable for biomedical applications. These radiolabeled protein substances are not denatured by the labeling process but retain their native physiobiological properties. This novel labeling technique provides a simple and rapid means of labeling plasma proteins such as human serum albumin, transferrin, lactoferrin, fibrinogen, and immunoglobulin or antibodies with $^{111}$In or $^{113m}$In for scintigraphic imaging which may allow visualization of thrombi, emboli, myocardial infarcts, infectious lesions, tumors or any vascular abnormalities in the body.

36 Claims, No Drawings

NOVEL PHYSIOLOGIC CHEMICAL METHOD OF LABELING PROTEIN SUBSTANCES WITH THE RADIONUCLIDES OF INDIUM

BACKGROUND OF THE INVENTION

Proteins are primary components of all living matter. They play crucial roles in virtually all biological processes. They may be classified according to biological function as the enzymes, hormones, the immunoglobulins or antibodies, the clotting proteins and the toxins. Other proteins that have less intense biological activity are the transport proteins, the storage proteins, the contractile and structure proteins. Many of these essential proteins are found in the circulating plasma. Thus, a simple and reliable method of labeling these substances with a suitable radionuclide which preserve their physiobiological properties offers unlimited potential in biomedical applications.

Despite the initial optimism over possible clinical application of radiolabeled proteins, the usefulness of these agents has been limited to mainly in in vitro clinical assays. Radioimmuno assays (RIA) using $^{125}$I-labeled antibodies has found a wide range of clinical applications in medicine. The versatility, sensitivity and accuracy of these RIA techniques are well documented in the medical literature. Attempts to use radiolabeled plasma proteins as scintigraphic imaging agents in Nuclear Medicine have been disappointing. There are only few radiolabeled plasma proteins commercially available for scintigraphic imaging purposes. These include $^{131}$I-labeled or $^{99m}$Tc-labeled human serum albumin(-HSA). Technetium-99m HSA is widely used in cardiology as a blood pool imaging agent, whereas, $^{131}$I-HSA has limited application in cisternography as an alternative to $^{111}$In-DTPA. HSA labeled with $^{125}$I has found useful application in blood volume determination as an adjunct to other clinical procedures. Although recent introduction of $^{125}$I-human fibrinogen has offered the clinicians a more sensitive means of detecting deep vein thrombosis, it is not a scintigraphic imaging agent. Because of the low energy gamma photon flux of $^{125}$I, the usefulness of radioiodinated fibrinogen is limited to surface counting technique on the lower extremities. A more wide spread use of radiolabeled plasma proteins in Nuclear Medicine has been severly restricted because of: (1) in vivo instability of radioiodinated proteins; (2) undesirable isotopic characteristics of the radionuclides used in the labeling process; (3) protein denaturation caused by the current labeling techniques; (4) potential danger of antigenic reaction and high risk of hepatitis transmission from radiolabeled exogenous plasma proteins.

Several critical parameters must be met before radiolabeled protein substances can be used as scintigraphic imaging agents. Among these are: (1) they must be stable and biologically active in the body; (2) they must be highly selective or specific for the targeted organ or lesion; (3) the radionuclide must be firmly bound to the protein ligand and stable for the duration of the study; (4) the radionuclide must have favorable isotopic characteristics that are compatible with conventional imaging equipments and finally, (5) these radiolabeled proteins must not be toxic or antigenic to human subjects.

Protein denaturation and complete loss of biological properties are the primary concern in protein labeling chemistry. Various techniques of labeling plasma proteins with $^{125}$I, $^{123}$I or $^{131}$I have been reported in the literature. The most commonly used chemical means is radioiodination of the protein in the presence of Chloromine-T or iodine monochloride. The labeling yields, however, is low and varies from 50–70%. In order to be clinically useful as radiopharmaceuticals, the desired labeled proteins must undergo a long and tedious separation and purification process. Radioiodinated proteins are unstable in vivo. The radionuclide is rapidly detached from the protein ligand caused by dehalogenation as evident by unusually high tissue background radioactivity observed in the scintigrams. Furthermore, there is increasing evidence that alternation of the protein molecular structure occurs during radioiodination.

Technetium-99m labeled human plasma proteins have not found wide acceptance in Nuclear Medicine. Although several plasma proteins such as HSA, fibrinogen, antibodies or antibody fragments have been labeled with $^{99m}$Tc by chemical means, only $^{99m}$Tc-HSA has been approved for human use. One major problem is that plasma proteins labeled by the current techniques either by Sn-acid reduction process at pH of less than 2 (U.S. Pat. No. 4,042,676 to Molinski et al, U.S. Pat. No. 4,094,965 to Layne and U.S. Pat. No. 4,311,688 to Rhodes) or by Sn-basic reduction method at pH 11.6 (U.S. Pat. No. 4,057,617 to Abramovici) are completely denatured with significant loss of physiobiologicaly properties. This renders them unsuitable for biomedical applications. HSA labeled with $^{99m}$Tc, for example, does not have the same native biological property as that of the unlabeled serum albumin. Thus, its usefulness has been limited to cardiac studies as a blood pool scintigraphic imaging agent. A second major obstacle which prevents a wider use of radiolabeled plasma proteins is the high risk of antigenic reaction due to denatured protein byproducts. To resolve these problems, the present inventor has developed a simple chemical method of labeling plasma proteins with $^{99m}$Tc under physiological condition (U.S. Pat. No. 4,293,537 to Wong). The basic labeling methodology involves the production of a stable and chemically active $^{99m}$Tc-(Sn)citrate complex species in neutral medium prior to the addition of the protein. The actual binding of $^{99m}$Tc to the protein ligand occurs at physilogic pH 7.4 condition, thus avoiding harsh treatment of the protein and preserving its native biological properties. (Wong DW, et al, J. Nucl. Med. 20:967, 1979 and Wong DW, et al, J. Nucl. Med. 23: 229, 1982).

Technetium-99m labeled plasma proteins which retain their natural biological properties after labeling are ideal scintigraphic imaging agents. Essentially, these radiolabeled protein substance will actively participate in the physiobiological processes in the body. Tc-99m labeled autologous antimicrobial or anti-tumor antibodies, for examples, are immunologically active against specific antigens. This provides a simple, unique and highly specific means of detecting infectious lesions or neoplasms. Similarly, diseases such as venous and arterial thrombosis, pulmonary or cerebral embolisms, myocardial infarction and tumors can be diagnosed using $^{99m}$Tc-labeled autologous human fibrinogen. One major disadvantage of $^{99m}$Tc-labeled compound is the isotopic characteristics of the radionuclide itself. Although $^{99m}$Tc has an ideal 140 KeV gamma photon flux compatible with existing scintigraphic imaging equipments, but it has a relatively short physical half-life of only 6 hours. This renders $^{99m}$Tc-based radiopharmaceuticals unsuitable for imaging studies that require observation period of more than 6 hours. A 24 hours delayed imaging study, for example, requires a dose of 25–50 mCi of the radiopharmaceutical. For imaging studies in excess of 24 hours, repeated injections are needed. However, the usefulness of radiolabeled plasma proteins can be extended considerably if they are labeled with a longer physical half-life radionuclide such as Indium-111($^{111}$In) or Gallium-67 ($^{67}$Ga) which has similar gamma photon energy.

Currently, there are only two medical useful radionuclides of Indium. These are $^{111}$In and $^{113m}$In. Of these, $^{111}$In possess the most ideal radioisotopic characteristics for scintigraphic imaging procedures. Indium-111 has a 2.83 days half-life and produces two gamma photons (173 and 247 KeV, respectively) per disintegration. Both of these are in a useful energy range for imaging with standard Nuclear Medicine equipments. The resultant 183% photon production per disintegration produces a very high photon flux per mCi administered. Because of its longer half-life, $^{111}$In-based radiopharmaceuticals are ideally suited for imaging studies that require observation period in days or weeks. Optimal delayed images can be obtained with a single injection of a small dose of the radiolabeled compound and yet produces minimal amount of radiation health hazard to patient. Indium-113m is also a pure gamma emitter which emits a 301 KeV gamma photon. However, it has a very short half-life of 1.65 hours. Indium-113m based radiopharmaceuticals are not suitable for imaging studies that require observation period of more than 3 hours.

Several indirect methods of labeling plasma proteins with $^{111}$In have been reported in the literature(Burchiel and Rhode, Radioimmunoimaging and Radioimmunotherapy, Elseier Science Publishing Co. N.Y., 1983). The most common technique requires the use of a bifunctional chelate, a compound which posses two binding sites; one site for chelating polyvalent metallic ion and a second site for coupling to the protein ligand. Basically, the chelate such ad EDTA(ethylenediamine tetraacetic acid) or DTPA(diethylenetriamine pentaacetic acid) is first converted to the acid anhydride form by reflux reaction with trifluoroacetic acid and thionyl chloride. A precipitate of EDTA-anhydride or DTPA-anhydride is formed and purified with anhydrous ether. The protein substance is then conjugated or coupled to the EDTA-anhydride or DTPA-anhydride by incubating the reaction mixture at 4° C. for 24 hours. The reaction mixture is then dialyzed at 4° C. for another 24 hours to remove chemical impurities, purified again by column chromatography and stored in a frozen state until needed for labeling. During labeling procedure, $^{111}$InCl$_3$ is added and is chelated to the EDTA- or DTPA-conjugated protein in an acidic pH 4 medium following a 2 hours room temperature incubation period. The radiolabeled product is again purified by gel column filtration to obtain the pure radiolabeled protein and to remove radiochemical impurities such as free or unbound $^{111}$In, $^{111}$In-DTPA and insoluble $^{111}$In-hydroxide colloids.

A closer examination of the bifunctional chelation labeling process reveals many flaws. This labeling process is extremely complicated, tedious and time consuming accompanying with very poor labeling yields. A binding or labeling efficiency ranging from 10–70% prior to purification process indicate that the bifunctional chelation technique is neither reliable nor reproducible. The primary problem is due to chemical decomposition of the cyclic anhydride caused by hydrolysis in the presence of air and moisture even at refrigeration temperature. Hydrolysis occurs more rapidly at room temperature causing complete decomposition of the cyclic anhydride. Thus, the coupling reaction of protein to cyclic anhydride must be carried out at 4° C. to avoid hydrolysis. The presence of hydrolyzed unconjugated DTPA or EDTA will compete with the protein ligand for the radionuclide resulting in reduced labeling yeilds. Since the labeling process takes place in room temperature at acidic pH condition, hydrolysis of the cyclic anhydride and denaturation of the protein will occur. Although proteins such as fibrinogen and antibodies labeled by this process have claimed to be biologically active, experimental evidence indicate that as much as 50% of the biological properties of the native protein is lost after labeling process (Scheinberg D. A., et al, Science 215: 1511, 1982 and Layne W. W., et al, J. Nucl. Med. 23: 627, 1982). The entire labeling process from the production of EDTA- or DTPA-anhydride protein conjugate to the actual coupling reaction with the radionuclide requires a minimum of 3–4 days. Extensive purification steps are needed to obtain pure radiolabeled protein. This increases the risk of microorganism and pyrogen contamination. The bifunctional chelation labeling process is neither simple, practical nor suitable for preparing pharmaceutically acceptable radiolabeled protein substances.

The present invention is the result of extensive investigation of the $^{99m}$Tc physiologic chemical labeling process developed by the present inventor. Experimental data confirm that the (Sn)citrate chemical species are capable of forming complex bimetallic chemical species with polyvalent metallic ions such as $^{99m}$Tc or $^{111}$In. These bimetallic complex species posses high protein binding property. They are also chemically active and stable at neutral pH 6–8 medium a condition is ideally suited for labeling protein substances.

The present invention offers many obvious advantages over the bifunctional chelation process for labeling plasma proteins with the radionuclides of Indium. Among these are: (1) the labeling process is a simple and a direct chemical method of incorporating the radionuclide to the protein ligand; (2) the labeling process is mild and without the use of toxic chemical reagents; (3) since plasma proteins are labeled under optimal physiologic pH 7.4 condition, their physiobiological properties are preserved. There is no evidence of protein denaturation or decomposition caused by the present labeling process; (4) the labeling yields is greater than 98% with excellent reliability and reproducibility; (5) the radionuclide is firmly bound to the protein ligand and free from radiochemical impurities; (6) the radiolabeled proteins are biochemically active and stable in excess 3 months period when properly stored at 2°–8° C.; (7) the radiolabeled protein is ready for use after labeling without the need of any purification steps, and finally, (8) the entire labeling process requires less than 1 hour of time and uses only few simple non-toxic chemicals. The present labeling process can be converted into an instant non-radioactive labeling reagent kit to facilitate in-house preparation of exogenous or autologous radiolabeled plasma protein injections.

SUMMARY OF THE INVENTION

Plasma proteins are labeled with the radionuclides of Indium by a novel physiologic chemical process. The labeling methodology requires the initial production of (Sn)citrate chemical species by the reaction of SnCl$_2$, SnF$_2$ or Sn-tartrate with sodium citrate in aqueous medium. This is followed by the formation of a bimetallic In-(Sn)citrate complex species at pH 7.4 via the reaction of (Sn)citrate with $^{111}$InCl$_3$ or $^{113m}$InCl$_3$ at 120° C. The resultant bimetallic complex species is stable and chemically active in neutral medium. In the presence of pure protein, the radionuclide $^{111}$In or $^{113m}$In binds tightly to the protein ligand at 37° C. forming an efficiently radiolabeled compound. The labeling yield is greater than 98% with less than 2% free or unbound radionuclide. These radiolabeled protein substances are stable and biochemically active in excess of 3 months when stored at 2°-8° C. There is no evidence of protein denaturation nor dissociation of the radionuclide from the protein ligand after a 3 months storage period. The entire labeling process which requires less than 1 hour of time produces a sterile pyrogen-free injection of radioactive tracer material ready for patient administration. No further purification of the final labeled product is necessary. This novel labeling technique will provide a simple mean of producing $^{111}$In- or $^{113m}$In-based radiopharmaceuticals suitable as scintigraphic imaging agents in Nuclear Medicine. Additionally, the present labeling process can be incorporated into a non-radioactive labeling reagent kit to facilitate the in-house preparation of radiolabeled exogenous or autologous plasma proteins.

DETAILED DESCRIPTION OF THE INVENTION

This invention is relates to the development of $^{111}$In-labeled plasma proteins useful as scintigraphic imaging agents in Nuclear Medicine. Specifically, it is a novel chemical method of labeling protein substances with the radionuclides of Indium, $^{111}$In or $^{113m}$In, producing a radiopharmaceutical suitable for radiologic diagnostic procedures. The invention further relates to the method of preparing prepackaged non-radioactive labeling reagent kit based on said labeling process and a simple method of using said kit for preparing radiolabeled exogenous or autologous human plasma proteins with generally available $^{111}$InCl$_3$ or $^{113m}$InCl$_3$ solution.

The basic methodology of the present labeling process requires the following sequential chemical reactions: (1) initial production of a (Sn)citrate chemical species by the reaction of stannous chloride (SnCl$_2$) with sodium citrate in aqueous medium; (2) formation of bimetallic In-(Sn)citrate complexing species at pH 7.4 with $^{111}$InCl$_3$ or $^{113m}$InCl$_3$ at 120° C.; 3) covalent binding of the radionuclide to the protein ligand at 37° C. Thus, in the present invention, the actual labeling of the protein with $^{111}$In or $^{113m}$In occurs at physiologic pH 7.4 condition. These radiolabeled proteins are not denatured and are ready for immediate use without any additional purification process.

In accordance with the principles of the present invention, the (Sn)citrate chemical species must be produced prior to the addition of radioactive indium trichloride (InCl$_3$). Addition of InCl$_3$ to either SnCl$_2$ solution or sodium citrate solution will prevent the formation of the intermediate (Sn)citrate chemical species which inturn inhibit the binding of the radionuclide to the protein ligand. Formation of the (Sn)citrate species can be accomplished by treating a solution of a tin salt such as stannous chloride (SnCl$_2$), stannous fluoride (SnF$_2$) or stannous tartrate with sodium citrate. Stannous chloride is preferred in the present embodiment. The stannous salt is dissolved in 0.05N hydrochloric (HCl) solution with a pH of less than 2. Addition of sodium citrate solution (pH 8.7) to the SnCl$_2$ solution will increase the pH of the reaction mixture to 6. At this pH condition, it is essential that an excess amount of sodium citrate is used to react with SnCl$_2$ to form the intermediate (Sn)citrate species and at the same time to provide a stable medium for InCl$_3$. In the absence of sodium citrate, InCl$_3$ will be precipitated from solution when the pH of the reaction medium increases above 3. The reaction mixture of SnCl$_2$ and sodium citrate is stirred & incubated at room temperature for 5 minutes to allow complete conversion of SnCl$_2$ to (Sn)citrate. Radioactive InCl$_3$ solution is then added to the (Sn)citrate solution and is stirred or shaken for 5 minutes. The pH of the radioactive admixture is raised to 7.4 with 0.1N sodium hydroxide (NaOH) solution. After pH adjustment, the radioactive admixture is then heated at 120° C. for 15 minutes to form the stable $^{111}$In-(Sn)citrate or $^{113m}$In-(Sn)citrate complex species and is allow to cool to room temperature prior to the reaction with the protein. The cooling period is essential since protein substances are easily denatured by heat. After cooling, an aqueous protein solution is then added slowly with gentle swirling to avoid foaming. The radioactive protein solution is then incubated at 37° C. for 30 minutes to catalyze the binding of the radionuclide to the protein ligand. Although covalent binding of the radionuclide to the protein ligand can proceed at room temperature, it requires a longer incubation period. The labeling yields, however, are similar under both conditions. For practical considerations, the 37° C. incubation temperature is preferred in the present invention.

The labeling mechanism is not well understood. Although not wise to be bound by theory, the radionuclide In is covalently bound to the protein ligand via the bimetallic In-(Sn)citrate complex species. Experimental data indicate that these chemical reactions of the present labeling process must be strictly followed for optimal binding of the radionuclide to the protein molecules. Furthermore, the presence of tin (Sn) is essential, for In-citrate alone will not bind to plasma proteins. The general procedure for labeling plasma proteins with the radionuclides of indium is as follows:

1. Treat a solution of SnCl$_2$ dissolved in 0.05N HCl with an excess amount of sodium citrate solution to form the (Sn)citrate chemical species;
2. React with the (Sn)citrate solution a radioactive solution of InCl$_3$ at room temperature for 5 minutes;
3. Raise the pH of the radioactive admixture to 7.4 with 0.1N NaOH solution;
4. Heat the neutralized radioactive admixture at 120° C. for 15 minutes to form the stable bimetallic In-(Sn)citrate complex species and allow it to cool to room temperature for 5-10 minutes;
5. Covalent binding of the radionuclide to the protein ligand by adding an aqueous protein solution to the radioactive In-(Sn)citrate solution and incubating at 37° C. for 30 minutes.
6. Cool the radiolabeled protein solution to room temperature before use or assay. Additional purification process of the labeled protein is unnecessary.

The amount of SnCl$_2$ required for the initial production of the (Sn)citrate chemical species depends on the quantity of the radionuclide used in the labeling process. This is normally ranged from 0.1 mg to 100 mg. The optimal amount of SnCl$_2$ needed for each batch or different quantity of radiolabeled protein can be determined by simple routine experiments by those who are skilled in the art. For the preparation of 0.1–100 mCi $^{111}$In- or $^{113m}$In-labeled protein, 0.1–5 mg of SnCl$_2$ is adequate. The stannous chloride reagent should be freshly prepared by dissolving the desired amount of SnCl$_2$.2H$_2$O powder or crystals in 6N HCl and diluted with distilled water to a final concentration of 0.2 mg/ml 0.05N HCl solution (pH <2). The stannous chloride solution is sterilized by passage through a 0.22 nm biological filter and injected into individual sterile, apyrogenic serum vial. Each vial containing 0.5 ml (0.1 mg) of the sterile SnCl$_2$ solution will serve as the reaction vial in the initial labeling process. Alternatively, the contents of the reaction vials can be kept in a frozen state until use. These vials are preferably lyophilized by conventional freeze-drying techniques to remove water and purged with nitrogen. This provides a solid mixture of SnCl$_2$ and 0.05N HCl which aids in shipping and storage and is more stable than in liquid reagent form. The lyophilized product can be restored to the original form by the addition of distilled water.

The amount of sodium citrate needed to form the (Sn)citrate chemical species varies depending on the quantity of SnCl$_2$ used in the initial reaction. In the present invention, 20–100 mg of sodium citrate is sufficient to treat 0.1–10 mg of SnCl$_2$ and to prevent the precipitation of the radioactive InCl$_3$. Sodium citrate solution is prepared by dissolving reagent grade trisodium citrate powder or crystals in distilled water to a concentration of 1–10%. In the preferred embodiment, 0.4 ml of a 5% sodium citrate solution is adequate to react with 0.1–5 mg SnCl$_2$. The sodium citrate solution is stable at room temperature or at 2°–8° C. for up to 2 years when properly prepared and stored. Preferably, this reagent is prepared and packaged in the form of a freeze-dried solid. The freeze-dried solid of sodium citrate can be reconstituted with distilled water at time of use.

Experimental data have confirmed that the (Sn)citrate chemical species formed by the reaction of SnCl$_2$ and sodium citrate is stable in aqueous neutral medium in room temperature or at 2°–8° C. Thus, the reaction mixture of SnCl$_2$ and sodium citrate can be combined and packaged as a single reagent either in liquid form or in the form of a lyophilized solid. The latter must be reconstituted with distilled water at time of use. It is essential that the formulation of this combined reagent must have the proper amount of active ingredients to react with the radionuclide. This can be determined by simple routine experiments by those who are skilled in the art.

The source of indium radionuclides should be water-soluble with the preferred source being radioactive indium trichloride (InCl$_3$). Indium-111 is available as $^{111}$InCl$_3$ dissolved in 0.05N HCl. $^{113m}$InCl$_3$ can be obtained by eluting a $^{113}$Sn-$^{113m}$In generator with 0.05N HCl solution. Both preparations are acidic with a pH of less than 3. Indium trichloride is stable only in acidic medium. Increasing the pH of the medium above 3 with dilute alkali such as 0.1N NaOH will convert the trichloride salt into insoluble In(OH)$_3$ colloids. This, however, can be prevented by the addition of sodium bicarbonate, sodium acetate or sodium citrate to the reaction medium prior to pH adjustment or prior to the addition of radioactive InCl$_3$. Since excess sodium citrate is used in the initial (Sn)citrate reaction, there is sufficient amount of sodium citrate remained in the reaction medium to prevent the precipitation of the radionuclide. Addition of other protective agents such as sodium bicarbonate or sodium acetate is unnecessary. Because of a more favorable half-life, $^{111}$In is preferred over $^{113m}$In in the present invention. The amount of $^{111}$In radioactivity requires in the present labeling process can vary from 0.1 mCi(millicurie) to 100 Ci (Curie) depending on the amount of protein desired to be labeled with the radionuclide. High specific concentration in term of mCi/mg of $^{111}$In-labeled protein can be obtained by adjusting the formulation of the active ingredients in the labeling process. This can be achieved by simple routine experiments by those who are skilled in the art.

Any dilute alkaline solution or pharmaceutically acceptable buffer systems having a pH above 8 may be used for pH adjustment of the $^{111}$In-(Sn)citrate complex solution. A dilute solution of 0.1N NaOH solution is preferred in the present embodiment because it is physiobiochemically compatible with many protein substances. The amount of dilute 0.1N NaOH solution needed for the preparation of up to 25 mCi of radiolabeled protein is normally less than 1 ml. For the preparation of bulk multi-curies quantity of $^{111}$In-(Sn)citrate complex solution, a more concentrated solution of 0.5–1.0N NaOH should be used to limit the volume of alkali needed for pH adjustment.

Experimental data have confirmed that the $^{111}$In-(Sn)citrate complex species formed after heating at 120° C. for 15 minutes is stable in aqueous neutral pH 7.4 medium. Thus, such a radioactive solution can be manufactured in bulk quantity in excess of 100 Ci prior to labeling different protein substances. The amount of active ingredients required to produce such a high concentration radioactive solution can be determined by simple routine experiments by those who are skilled in the art. The $^{111}$-In-(Sn)citrate solution is sterilized by conventional sterilization techniques or by ultrafiltration process and stored either at room temperature or at 2°–8° C. until needed. Alternatively, aliquot amount of the bulk radioactive solution in 3, 5, 10 or 25 mCi unit can be prepared and packaged in sterile apyrogenic containers for distribution and sales. This facilitates the in-house preparation of autologous or exogenous plasma proteins so desired by the user.

The amount of protein that can be labeled with the radionuclides of Indium varies from 0.1 mg to 10 grams. In the present invention, a concentration of 0.1 mg–100 mg of protein dissolved in 0.5–1.0 ml diluent is adequate to bind up to 100 mCi of $^{111}$In or $^{113m}$In. Any pharmaceutically acceptable diluents such as distilled water, normal saline (0.9% NaCl) or biological buffer having a neutral pH can be used to dilute or to reconstitute the protein to the desired concentrations. For preparing multi-curies quantity of exogenous radiolabeled proteins such as HSA, human lactoferrin and human transferrin, the protein requirement can exceed 10 grams. These radiolabeled products should be stored at refrigeration temperature either in liquid forms or as lyophilized solids. Pharmaceutically acceptable preservatives or stabilizers should be added after labeling process to maintain proper sterility and apyrogenicity.

In order to demonstrate the efficacy of the present invention, several plasma proteins have been labeled with $^{111}$In with consistant high labeling yields. These includes human serum albumin, human immune gamma globulin, human transferrin, human lactoferrin, autologous human fibrinogen and the enzyme bovine thrombin. All exogenous protein preparations are prepared according to manufacturer's direction and diluted to a concentration of 1–5 mg/ml with pH 7.4 Sorenson's 7 mM phosphate buffer. Autologous human fibrinogen is obtained from human plasma by a modified glycine extraction process of Kazal and redissolved in pH 7.4 phosphate buffer (Kazal LA, et al, Proc. Soc. Exptl. Biol. Med. 113:989, 1963).

The binding efficiency or labeling yield of the various radiolabeled proteins was assessed by ascending paper radiochromatography with Whatman No. 1 paper and thin layer radiochromatography with ITLC-SG plates developed in 0.1N HCl-acetone (1:1) solvent system. Radiolabeled protein remains at the origin of the chromatogram (Rf=0.0), whereas, free or unbound $^{111}$In or $^{113m}$In migrates toward the solvent front with a Rf value of 1.0. The actual amount of radiolabeled protein was determined by protein precipitation method with 20% trichloroacetic acid(TCAA) in the presence of unlabeled carrier protein. In vitro assessment of the biochemical properties of the radiolabeled fibrinogen and thrombin consisted of clottability assay with enzyme or protein substrates. In case of $^{111}$In-labeled fibrinogen, 10 units of the enzyme bovine thrombin was added to clot the fibrinogen prior to TCAA assay in order to determine the actual amount of clottable protein present in the labeled product. For $^{111}$In-thrombin, human fibrinogen was used as the substrate to determine the enzymatic activity of the radiolabeled enzyme.

Qualitative radioactive protein identification was determined by protein electrophoresis using cellulose polyacetate support medium. Samples from each batch of radiolabeled protein were assayed before and after incubating in human serum at 37° C. for 24 hours. Any dissociation or translocation of the radionuclide from the protein ligand could be detected by this technique. Additionally, these radiolabeled products were subjected to gel column filtration analyses with high molecular weight gel column. Stability determination of the final labeled products was assessed by TCAA preciipitation method and in vitro biochemical assays. Samples from each batch were monitored up to 3 months period first by assaying $^{111}$In radioactivity in the samples followed by assessment of the $^{114}$In activity. Radiopharmaceutical grade $^{111}$InCl$_3$ solution is only 99% pure with $^{114}$In and $^{65}$Zn as major radiocontaminants. $^{114}$In has a half-life of 50 days and a gamma photon flux of 192 KeV energy which can be discriminated from the 1.115 MeV $^{65}$Zn in the gamma scintillation counter. Since all radioisotopes of the same element have identical chemical properties, $^{114}$In also binds to the protein by the labeling process. Thus, by assaying $^{114}$In-labeled protein, the stability determination of the labeled products can be extended to months rather than days.

Results from radioanalyses confirmed that the radionuclide was indeed tightly bound to the protein ligand with no evidence of protein denaturation or loss of biological properties after labeling process. All radiolabeled proteins were eluted from the gel column in the void volume identical to that of unlabeled proteins, an indication that the radionuclide was firmly bound to the protein molecules. Unlike unlabeled plasma proteins, $^{111}$In-labeled proteins did not migrate in electrical field but remained at the origin of the electrophoretic plate. However, after incubating in human serum at 37° C. for 24 hours, the radionuclide remained bound to the protein ligand. There was no evidence of dissociation or translocation of the "label" to other protein fractions in the serum. Data from radioanalyses were similar with the average labeling yield of greater than 98% as assessed by TCAA precipitation method and by paper and TLC radiochromatography. Free or unbound $^{111}$In was less than 2%. Both $^{111}$In-labeled fibrinogen and thrombin were biochemically active with their respective substrate in vitro. After clotting with the enzyme thrombin, greater than 95% of $^{111}$In-fibrinogen was detected in the clot with a clottability of 97.5%. Radiolabeled enzyme bovine thrombin was biologically active after labeling with $^{111}$In. Data from biochemical assay demonstrated that the enzymatice activity of $^{111}$In-thrombin exceeded 92%. All radiolabeled proteins were stable in excess of 3 months when stored at refrigeration temperature of 2°–8° C. These labeled products remained biochemically active after 3 months storage period further documenting the efficacy of the present labeling process.

The present invention is not limited to labeling plasma proteins with the radionuclides of Indium. Any compounds or substances that contain protein moiety such as glycoproteins, lipoproteins, hemoglobin, collagen, myoglobulin, protein enzymes and protein hormones can be labeled with $^{111}$In or $^{113m}$In by the present labeling process. It is essential that these protein substances are dissolved in aqueous neutral media such as distilled water, normal saline or suitable biological buffers. Any pharmaceutically acceptable preservatives can be added to stabilize these protein solutions.

Protein substances labeled with the radionuclides of Indium that are biologically active are ideal scintigraphic imaging agents. Essentially, these radiolabeled tracers will actively incorporated into the biochemical processes in the body. $^{111}$In-labeled human fibrinogen, for example, is extremely useful for localizing and detecting blood clots of the deep veins, in thromboembolic disorders such as pulmonary or cerebral embolism, in myocardial infarction or neoplasms using scintigraphic imaging technics. Similarly, infectious lesions and tumors can be specifically detected with $^{111}$In-labeled autologous immunoglobulins or monoclonal antibodies. Radiolabeled proteins such as enzymes, hormones and lactoferrin may find useful clinical applications in tumor detection of the breast, endocrine glands and the lymphatic system. Other useful applications include the use of $^{111}$In-HSA as blood pool imaging agent for placenta localization, nuclear cardiology and cisternography and $^{111}$In-transferrin for bone marrow evaluation. Of special medical interest is to use these radioactive tracers in localization and detection of abnormal bleeding sites or hemmorrhage in the lungs and gastrointestinal tracts. In general, a tracer dose of 0.1 mCi to 5 mCi of the radiolabeled protein administered intravenously to patient is sufficient to detect these lesions as described above. The usual dosage should be determined based on the age and body weight of each patient. Whole body scintigrams or images are taken at various time intervals, e.g. from 0.5 to 24 hours post administration of the dose using a rectilinear scanner or an Anger camera. Increased radioactivity at the sites of these lesions indicates the presence of thrombi, emboli, myocardial infarcts, infectious foci, tumors or other vascular abnormalities. Since $^{111}$In has a favorable half-life of 3 days, a single injection of $^{111}$In-radiopharmaceutical is adequate to monitor or to scan the patient daily for weeks to follow the course of the disease. For imaging study that requires observation period beyond two weeks, a higher dose in excess of 5 mCi of the radiolabeled protein is recommended.

The present invention is far superior to previous reported labeling techniques. Based on the chemical labeling process described above, a simple non-radioactive labeling reagent kit can be prepared in advance with individual components packaged separately in sealed, sterile, apyrogenic containers. The labeling reagent kit is comprised of 4 basic components: (1) an aqueous solution of tin salt such as $SnCl_2$, $SnF_2$ or stannous tartrate dissolved in 0.05N HCl; (2) an aqueous solution of 5% sodium citrate; (3) a dilute alkaline solution such as 0.1N NaOH for pH adjustment and (4) an aqueous protein solution. Alternatively, the labeling reagent kit can be reduced to 3 basic components by combining $SnCl_2$ with sodium citrate as a single reagent. This is done by treating a solution of $SnCl_2$ dissolved in 0.05N HCl with sodium citrate prior to packaging. The resultant (Sn)citrate solution is stable and chemically active in aqueous medium which can be incorporated into the labeling reagent kit as such. In either case, the labeling reagent kit is to be used in conjunction with a source of $^{111}InCl_3$ or $^{113m}InCl_3$ solution. With the exception of human fibrinogen and antibodies, exogenous protein preparations are commercially available in sterile apyrogenic solution or in lyophilized solid forms. These commercial protein preparations can be repackaged in small quantities and incorporated into the labeling reagent kit. Antimicrobial and anti-tumor polyclonal antibodies must be isolated and extracted from patient's own serum. These proteins are produced only in patients who are afflicted with infection or tumors. They are chiefly gamma globulins in composition which can be divided further into subgroups as IgG, IgE, IgM, IgA or IgD. The antibody activity or titre increases dramatically as a result of bacterial, fungal, yeast or viral infections. The presence of malignant tumor such as melanoma or bronchogenic carcinoma can also cause the production of antibodies within the host in response to the insult. These antimicrobial and anti-tumor antibodies can easily be isolated and extracted from serum by a modified rivanol(2-ethoxy 6,9-diaminacridine lactate) fractionation method of Horejsi and Smetana (Horejsi J. and Smetana R., Acta. Med. Scand. 155:65, 1956), Monoclonal antibodies represent an alternate source of highly pure and highly specific immunogens. These antibodies when labeled with a suitable radionuclide are extremely useful in radioimmunoimaging and radioimmunotherapy.

The principal objective of the labeling reagent kit is to provide a simple means of labeling any protein substances so desired by the user with any radionuclides of Indium based on the present labeling process. With the availability of such a kit, the user can also label autologous plasma proteins such as fibrinogen and antibodies whenever is needed. Thus, such a simple labeling reagent kit will provide the user an easy access to the present chemical labeling process and to produce sterile radioactive diagnostic compositions suitable for use in scintigraphic imaging procedures.

In use, the labeling reagent kit of the present invention is mixed with solution of either $^{111}InCl_3$ or $^{113m}InCl_3$ to form an efficiently radiolabeled protein suitable as scintigraphic imaging agent. The radiolabeled protein of the present invention is prepared and readied for injection in a simple 5-steps procedures. In the first step, 0.4 ml (20 mg) sodium citrate solution is withdrawn into a syrine and is injected into the reaction vial containing the $SnCl_2$ solution. The contents of the reaction vial is shaken for 1-5 minutes to allow complete formation of the (Sn)citrate chemical species. In the second step, a sufficient amount of radioactive $InCl_3$ solution providing 0.1-100 mCi of radioactivity is injected into the reaction vial and shaken 1-5 minutes. In the third step, raise the pH of the radioactive admixture to 7.4 with 0.1N NaOH solution. In the fourth step, the neutralized radioactive admixture is heated at 120° C. for 15 minutes to form the bimetallic radioactive In-(Sn) citrate complex species and allow it to cool to room temperature for 5-10 minutes. In the fifth step, 1 ml of the protein solution providing 0.1-5 mg of protein is aseptically injected into the reaction vial containing the neutralized radioactive admixture from step (4) and is allowed to incubate at 37° C. for 30 minutes. After incubation and cooled to room temperature, the radiolabeled protein preparation is ready for injection without any additional purification steps.

The following examples illustrate the simplicity and efficacy of the present invention for labeling various protein substances with the radionuclides of Indium.

EXAMPLE 1

Protein formulation

1. Human serum albumin, salt poor, 5% or 25% solution diluted with pH 7.4 phosphate buffer or normal saline to a concentration of 1-10 mg/ml.
2. Human transferrin, reconstituted with pH 7.4 phosphate buffer to a concentration of 1-10 mg/ml.
3. Human lactoferrin, reconstituted with pH 7.4 phosphate buffer to a concentration of 1-10 mg/ml.
4. Autologous or exogenous human fibrinogen, redissolved in pH 7.4 phosphate buffer to a concentration of 1-5 mg/ml.
5. Autologous or exogenous immune gamma globulin or antibody dissolved in pH 7.4 phosphate buffer to a concentration of 1-5 mg/ml.
6. Bovine thrombin, reconstituted with pH 7.4 phosphate buffer or normal saline to a concentration of 1000 units/ml.

EXAMPLE 2

General procedure for labeling plasma proteins with $^{111}In$ or $^{113m}In$

1. Inject 0.4 ml (20 mg) of a 5% sodium citrate solution into the reaction vial containing 0.5 ml of a solution of 0.1-5 mg $SnCl_2$ dissolved in 0.05N HCl. Mix the contents of the reaction vigorously for 1 minute and allow to incubate at roomm temperature for additional 4 minutes to form the (Sn)citrate chemical species.
2. Add a radioactive solution of either $^{111}InCl_3$ or $^{113m}InCl_3$ providing from 0.1-100 mCi of radioactivity to the reaction admixture of step (1) and shake vigorously for 1-5 minutes.
3. Raise the pH of the radioactive admixture of step (2) to 7.4 with 0.1N NaOH solution.
4. Heat the neutralized radioactive admixture of step (3) at 120° C. for 15 minutes and allow it to cool to room temperature for 5-10 minutes
5. Inject 1 ml (0.1-100 mg) of any protein solution desired to be labeled into the reaction vial slowly with gentle mixing to avoid foaming.
6. Incubate the contents of the reaction vial containing the radioactive protein admixture at 37° C. for 30 minutes and allow it to cool to room temperature for 5-10 minutes after incubation period. The final labeled product is clear and ready for use. Additional purification process of the radiolabeled protein is unnecessary.
7. Perform qualitative and quantitative radioactive assays.
8. For scintigraphic imaging, a dose of 0.1–5 mCi radiolabeled protein is sufficient to detect various types of lesion by scanning the patient with a rectilinear scanner or an Anger scintillation camera and by observing areas of increased radioactivity at the sites of these abnormalities as seen in the scintigrams.

EXAMPLE 3

Formulation of the non-radioactive labeling reagent kit for preparing $^{111}$In-labeled or $^{113m}$In-labeled plasma protein injection.

Essentially, the labeling reagent kit consists of 4 basic components each aseptically prepared and packaged separately in sterile apyrogenic serum vials. When properly prepared, lyophilized and stored at 2°–8° C., such a labeling reagent kit is stable for more than 2 years.

Vial #1; Stannous chloride reagent: Each vial containing 0.1–5 mg of $SnCl_2$ dissolved in 0.05N HCl solution serves as the reaction vial for the entire labeling process. The content of the vial is lyophilized and stored under nitrogen for longer shelve life. The lyophilized solid is to be reconstituted with 0.5–1.0 ml Water for Injection at time of use.

Vial #2; Sodium citrate reagent: Each vial contains 1–5 ml of an aqueous solution of 5% sodium citrate. The content of the vial is lyophilized and stored under nitrogen. This reagent is to be reconstituted with 1–5 ml Water for Injection at time of use.

Vial #3; Dilute alkaline solution: Each vial contains 1–5 ml of an aqueous solution of 0.1N NaOH. This reagent can be packaged either in liquid form or in the form of a freeze-dried solid. The latter must be reconstituted with same volume of Water for Injection at time of use.

Vial #4; Plasma protein solution: Each vial contains 0.1–100 mg of protein dissolved in aqueous medium such as normal saline, distilled water or phosphate buffer having a pH of 7–7.4 and properly preserved with any pharmaceutically acceptable preservatives or stabilizing agents. The protein solution can be packaged either in liquid or lyophilized form.

EXAMPLE 4

Procedure for preparing $^{111}$In- or $^{113m}$In-labeled plasma protein injection utilizing the labeling reagent kit of Example 3.

The directions outlined below must be strictly followed for optimal preparation of radiolabeled plasma protein injection. Aseptic technique must be observed through out the entire labeling procedure. Remove the reagent kit from the refrigerator and warm to room temperature before continuing.

1. Reconstitute the lyophilized $SnCl_2$ reagent of Vial #1 with 0.5–1.0 ml Water for Injection until completely dissolved.
2. Reconstitute the sodium citrate reagent of Vial #2 and 0.1N NaOH in Vial #3 each with 1–5 ml Water for Injection until completely dissolved.
3. Reconstitute the content of Vial #4 which contains the plasma protein desired to be labeled with the radionuclide in Water for Injection or normal saline to a concentration of 0.1–10 mg/ml.
4. Aseptically withdraw 0.4 ml of the sodium citrate solution into a syringe and injected into the reaction Vial #1 containing the $SnCl_2$ reagent. Shake the contents of the reaction vial for 1–5 minutes.
5. Inject a radioactive solution of either $^{111}$InCl$_3$ or $^{113m}$InCl$_3$ providing 0.1–100 mCi of radioactivity into the reaction mixture of step (4) and shake vigorously for 1–5 minutes.
6. Raise the pH of the radioactive admixture of step (5) to 7.4 with a sufficient amount of 0.1N NaOH solution.
7. Heat the neutralized radioactive admixture of step (6) at 120° C. for 15 minutes and allow it to cool to room temperature for 5–10 minutes.
8. Inject 1 ml of the reconstituted protein solution into the reaction vial containing the neutralized radioactive In-(Sn)citrate complex species slowly with gentle mixing to avoid foaming.
9. Incubate the contents of the reaction vial containing the radioactive protein admixture at 37° C. for 30 minutes and allow it to cool to room temperature for 5–10 minutes after incubation period.
10. Perform qualitative and quantitative radioactive assays.

The above examples and detailed described procedures are for illustration purposes only and are not intended to be limiting of the scope of the invention. It will be apparent to those skilled in the art that both may be modified within the scope of the invention defined in the following claims.

I claim:

1. A method of labeling mammalian plasma proteins with the radionuclides of Indium at physiologic pH 6–8 condition which comprises the sequential steps of:
   a. mixing a solution of stannous salt with an aqueous solution of sodium citrate at room temperature for 1–5 minutes;
   b. reacting the (Sn)citrate chemical species of step (a) with a radioactive solution of InCl$_3$ at room temperature for 1–5 minutes;
   c. raising the pH of the radioactive mixture of step (b) to 7.4 with a sufficient amount of dilute alkaline solution;
   d. heating the neutralized radioactive admixture of step (c) at 120° C. for 15 minutes and allow it to cool to room temperature for 5–10 minutes;
   e. binding of the radionuclide to the protein ligand by adding an aqueous protein solution desired to be labeled to the neutralized radioactive admixture of step (d) and incubating the radioactive protein admixture at 37° for 30 minutes.

2. A method according to claim 1, wherein said radionuclides of Indium is selected from the group consisting of $^{111}$In, $^{113m}$In and $^{114}$In.

3. A method according to claim 2, wherein said radionuclide of Indium is an aqueous solution of $^{111}$InCl$_3$, $^{113m}$InCl$_3$ or $^{114}$InCl$_3$ providing from 0.1 mCi to 100 Ci of radioactivity.

4. A method according to claim 1, wherein said stannous salt is selected from the group consisting of stannous chloride($SnCl_2$), stannous fluoride ($SnF_2$) and stannous tartrate.

5. A method according to claim 4, wherein said stannous salt is present in the amount of 0.1–100 mg dissolved in 0.05–0.1N HCl solution.

6. A method according to claim 5, wherein said stannous salt is present in the amount of 0.2–5 mg per ml of 0.05N HCl solution.

7. A method according to claim 1 wherein said sodium citrate solution is an aqueous solution of 0.5–10% trisodium citrate.

8. A method according to claim 7 wherein said sodium citrate solution is an aqueous solution of 5% trisodium citrate.

9. A method according to claim 1 wherein said dilute alkaline solution is an aqueous solution of 0.1–1.0N NaOH.

10. A method according to claim 9, wherein said dilute alkaline solution is an aqueous solution of 0.1N NaOH.

11. A method according to claim 1, wherein said plasma protein is selected from the group consisting of human serum albumin, human transferrin, human lactoferrin, human fibrinogen, human immune gamma globulin and bovine thrombin.

12. A method according to claim 11, wherein said plasma protein is present in the amount of 0.1 mg to 10 grams dissolved in aqueous medium together with any pharmaceutically acceptable preservatives or stabilizing agents.

13. A method according to claim 12, wherein said plasma protein is present in the amount of 0.1–100 mg dissolved in 1–5 ml distilled water or normal saline.

14. A method of producing a protein binding radioactive bimetallic compound of Indium having a formulus of $M(Sn)C_6H_5O_7$ where M=In-111, In-113m or In-114 at physiologic pH 6–8 condition which comprises the sequential steps of:
  a. mixing a solution of stannous salt with an aqueous solution of sodium citrate at room temperature for 1–5 minutes;
  b. reacting the (Sn)citrate chemical species of step (a) with a radioactive solution of $InCl_3$ at room temperature for 1–5 minutes;
  c. raising the pH of the radioactive mixture of step (b) to 7.4 with a sufficient amount of dilute alkaline solution;
  d. heating the neutralized radioactive admixture of step (c) at 120° C. for 15 minutes and allow it to cool to room temperature for 5–10 minutes.

15. A method according to claim 14, wherein said radionuclides of Indium is selected from the group consisting of $^{111}In$, $^{113m}In$ and $^{114}In$.

16. A method according to claim 15, wherein said radionuclide of Indium is an aqueous solution of $^{111}InCl_3$, $^{113m}InCl_3$ or $^{114}InCl_3$ providing from 0.1 mCi to 100 Ci of radioactivity.

17. A method according to claim 14, wherein said stannous salt is selected from the group consisting of stannous chloride, stannous fluoride and stannous tartrate.

18. A method according to claim 17, wherein said stannous salt is present in the amount of 0.1–100 mg dissolved in 0.05–0.1N HCl solution.

19. A method according to claim 18, wherein said stannous salt is present in the amount of 0.2–5 mg per ml 0.05N HCl solution.

20. A method according to claim 14, wherein said sodium citrate solution is an aqueous solution of 0.5–10% trisodium citrate.

21. A method according to claim 20, wherein said sodium citrate solution is an aqueous solution of 5% trisodium citrate.

22. A method according to claim 14, wherein said dilute alkaline solution is an aqueous solution of 0.1–1.0N NaOH.

23. A method according to claim 22, wherein said dilute alkaline solution is an aqueous solution of 0.1N NaOH.

24. A method of labeling mammalian plasma proteins with $^{111}InCl_3$ at physiologic pH 6–8 condition comprising the sequential steps of:
  a. mixing a solution of 0.1 to 5.0 mg of $SnCl_2$ dissolved in 0.05N HCl with 0.4 ml of a 5% sodium citrate solution at room temperature for 1–5 minutes;
  b. reacting the (Sn)citrate chemical species from step (a) with a solution of $^{111}InCl_3$ providing 0.1–100 mCi of radioactivity at room temperature for 1–5 minutes;
  c. raising the pH of the radioactive mixture of step (b) to 7.4 with a sufficient amount of 0.1N NaOH solution;
  d. heating the neutralized radioactive admixture of step (c) at 120° C. for 15 minutes and allow it to cool to room temperature for 5–10 minutes;
  e. adding from 0.1 mg to 100 mg of the desired protein to be labeled in 1–5 ml diluent to the radioactive admixture of step (d) and incubating said radioactive protein admixture at 37° C. for 30 minutes.

25. A method according to claim 24, wherein said plasma protein is selected from the group consisting of human serum albumin, human transferrin, human lactoferrin, human fibrinogen, human immune gamma globulin and bovine thrombin.

26. A method according to claim 24, wherein said human serum albumin is labeled with $^{111}In$.

27. A method according to claim 24, wherein said human transferrin is labeled with $^{111}In$.

28. A method according to claim 24, wherein said human lactoferrin is labeled with $^{111}In$.

29. A method according to claim 24, wherein said human fibrinogen is labeled with $^{111}In$.

30. A method according to claim 24, wherein said human immune gamma globulin is labeled with $^{111}In$.

31. A method according to claim 24, wherein said bovine thrombin is labeled with $^{111}In$.

32. A method of detecting vascular abnormalities in the body of a mammal by scintigraphic imaging techniques comprising:
  a. administering intravenously to said mammal from 0.1 mCi to 5 mCi of $^{111}In$-serum albumin labeled according to the method of claim 24;
  b. scanning said mammal with a scintillation camera or a rectilinear scanner at various time intervals from 0.5 to 24 hours and daily for up to two weeks;
  c. observing areas of increased radioactivity at the sites of the abnormality as seen in the scintigrams.

33. A method of detecting bone marrow abnormality in man or in animal by scintigraphic imaging techniques comprising:
  a. administering intravenously to said mammal from 0.1 mCi to 5 mCi of $^{111}In$-transferrin labeled according to the method of claim 24;
  b. scanning said mammal with a scintillation camera or a rectilinear scanner at various time intervals from 0.5 to 24 hours and daily for up to two weeks;
  c. observing increasing or decreasing radioactivity in the reticuloendothelial system as seen in the scintigrams.

34. A method of localizing and detecting fibrin clot deposition in thromboembolic diseases, myocardial infarction or tumors in man or in animal by scintigraphic imaging procedures comprising:

a. administering intravenously to said mammal from 0.1 mCi to 5 mCi of $^{111}$In-fibrinogen labeled according to the method of claim 24;
b. scanning said mammal with a scintillation camera or a rectilinear scanner at various time intervals from 0.5-24 hours and daily for up to two weeks;
c. observing increasing radioactivity accumulated at the sites of these lesions as seen in the scintigrams.

35. A method of localizing and detecting infectious foci in man or in animal by scintigraphic imaging procedures comprising:
a. administering intravenously to said mammal from 0.1 mCi to 5 mCi of $^{111}$In-immunoglobulin labeled according to the method of claim 24 which contains the specific antibody against the antigen or microorganism;
b. scanning said mammal with a scintillation camera or a rectilinear scanner at various time intervals from 0.5-24 hours and daily for up to two weeks;
c. observing increasing radioactivity accumulated at the sites of the infection as seen in the scintigrams.

36. A method of localizing and detecting benign or malignant tumors in man or in animal by scintigraphic imaging techniques comprising:
a. administering intravenously to said mammal from 0.1 mCi to 5 mCi of $^{111}$In-immunoglobulin labeled according to the method of claim 24 which contains the specific antibody against the specific tumor;
b. scanning said mammal with a scintillation camera or a rectilinear scanner at various time intervals from 0.5-24 hours and daily for up to two weeks;
c. observing increasing radioactivity accumulated at the sites of thes tumors as seen in the scintigrams.

* * * * *